(12) United States Patent
DiLoreto

(10) Patent No.: US 10,646,344 B2
(45) Date of Patent: May 12, 2020

(54) INFLATABLE PENILE PROSTHESIS WITH FOUR-WAY VALVE PUMP

(71) Applicant: Boston Scientific Scimed, Inc., Maple Grove, MN (US)

(72) Inventor: Mark Edward DiLoreto, Chaska, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 238 days.

(21) Appl. No.: 15/670,530

(22) Filed: Aug. 7, 2017

(65) Prior Publication Data

US 2018/0042724 A1    Feb. 15, 2018

Related U.S. Application Data

(60) Provisional application No. 62/373,719, filed on Aug. 11, 2016.

(51) Int. Cl.
*A61F 5/00* (2006.01)
*A61F 2/26* (2006.01)
*A61F 2/48* (2006.01)
*A61M 39/22* (2006.01)

(52) U.S. Cl.
CPC .......... *A61F 2/26* (2013.01); *A61F 2002/485* (2013.01); *A61M 39/22* (2013.01)

(58) Field of Classification Search
CPC .................................... A61F 2/26; A61F 5/41
USPC ..................................................... 600/38–41
See application file for complete search history.

(56) References Cited

U.S. PATENT DOCUMENTS

| | | | |
|---|---|---|---|
| 3,853,116 A | 12/1974 | Bucalo | |
| 3,954,102 A | 5/1976 | Buuck et al. | |
| 6,533,719 B2 | 3/2003 | Kuyava et al. | |
| 6,723,042 B2 | 4/2004 | Almli et al. | |
| 6,730,017 B2 | 5/2004 | Kuyava et al. | |
| 6,935,847 B2 | 8/2005 | Kuyava et al. | |
| 7,350,538 B2 | 4/2008 | Kuyava et al. | |

(Continued)

FOREIGN PATENT DOCUMENTS

| | | |
|---|---|---|
| WO | 2001/047441 A2 | 7/2001 |
| WO | 2017/165279 A1 | 9/2017 |

OTHER PUBLICATIONS

International Search Report and Written Opinion for PCT Patent Application No. PCT/US2017/045893, dated Dec. 8, 2017, 18 pages.

*Primary Examiner* — John P Lacyk
(74) *Attorney, Agent, or Firm* — Brake Hughes Bellermann LLP

(57) ABSTRACT

According to an aspect, an inflatable penile prosthesis includes an inflatable member, a reservoir configured to hold fluid, and a pump assembly configured to facilitate a transfer of the fluid from the reservoir to the inflatable member when in an inflation mode, and facilitate the transfer of the fluid from the inflatable member to the reservoir when in a deflation mode. The pump assembly may include a pump, and a valve body defining at least three ports operatively coupled to the pump such that three separate fluid channels extend to the pump. The valve body defines at least one port operatively coupled to the reservoir, and at least one port operatively coupled to the inflatable member. The pump assembly includes a spool configured to move within the valve body to switch between the inflation mode and the deflation mode.

19 Claims, 9 Drawing Sheets

(56) References Cited

U.S. PATENT DOCUMENTS

| | | | |
|---|---|---|---|
| 7,438,682 B2 | 10/2008 | Kuyava et al. | |
| 7,442,165 B2 * | 10/2008 | Forsell | A61F 2/26 600/38 |
| 8,276,591 B2 | 10/2012 | Kuyava et al. | |
| 2013/0072751 A1 | 3/2013 | Fogarty | |

* cited by examiner

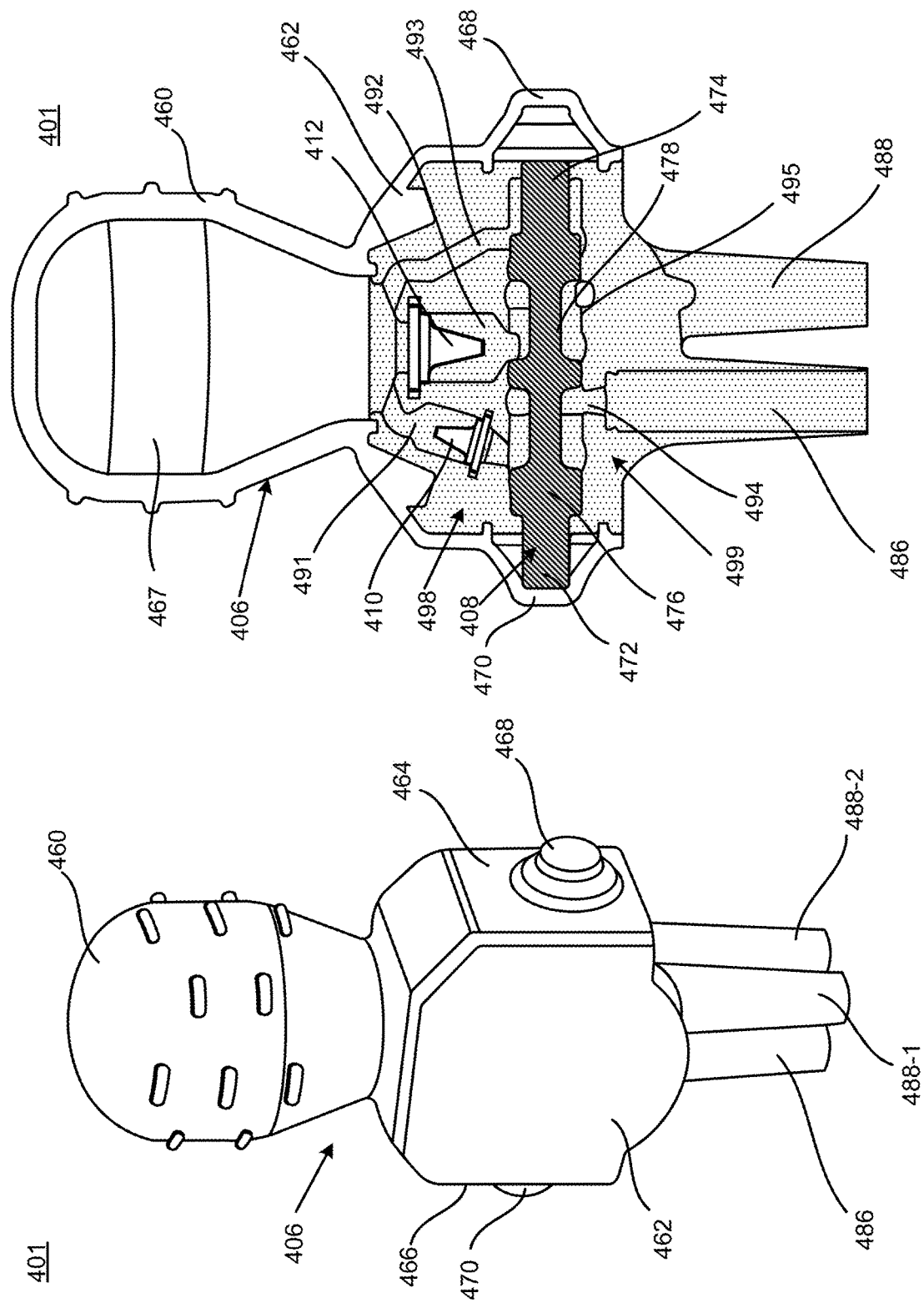

INFLATABLE PENILE PROSTHESIS WITH FOUR-WAY VALVE PUMP

CROSS-REFERENCE TO RELATED APPLICATION

This application is a Nonprovisional of, and claims priority to, U.S. patent application Ser. No. 62/373,719, filed on Aug. 11, 2016, entitled "INFLATABLE PENILE PROSTHESIS WITH FOUR-WAY VALVE PUMP", which is incorporated by reference herein in its entirety.

TECHNICAL FIELD

This disclosure relates to an inflatable penile prosthesis with a four-way valve pump and methods for operating the same.

BACKGROUND

One common treatment for male erectile dysfunction is the implantation of a penile prosthesis that mechanically erects the penis. According to some existing designs of inflatable penile prostheses, the amount of time, energy and disparity from the occurrence of a normal human male erection for the patient to inflate a penile prosthesis (e.g., the number of pumps and time required to provide the desired penis rigidity) may be relatively high, and additionally transitioning to the deflation state may be relatively cumbersome.

SUMMARY

According to an aspect, an inflatable penile prosthesis includes an inflatable member, a reservoir configured to hold fluid, and a pump assembly configured to facilitate a transfer of the fluid from the reservoir to the inflatable member when in an inflation mode, and facilitate the transfer of the fluid from the inflatable member to the reservoir when in a deflation mode. The pump assembly may include a pump, and a valve body defining at least three ports operatively coupled to the pump such that three separate fluid channels extend to the pump. The valve body defines at least one port operatively coupled to the reservoir, and at least one port operatively coupled to the inflatable member. The pump assembly includes a spool configured to move within the valve body to switch between the inflation mode and the deflation mode.

According to various aspects, the inflatable penile prosthesis may include one or more of the following features (or any combination thereof). The three separate fluid channels defined by the valve body may include a first fluid channel, a second fluid channel, and a third fluid channel. The pump assembly may include a first check valve disposed within the first fluid channel, and a second check valve disposed within the second fluid channel. The third fluid channel may be devoid of a check valve. The pump may include a pump bulb. The spool may be configured to be manually operated by a user of the inflatable penile prosthesis. The pump may include a pump bulb and a valve body connector integrally formed with the pump bulb, where the valve body connector defines a cavity, and at least a portion of the valve body is disposed within the cavity of the valve body connector. The spool may include an elongated member having a plurality of enlarged portions and a plurality of reduced portions, where at least one of the plurality of enlarged portions is configured to block at least one of the three separate fluid channels in the inflation mode and the deflation mode. The valve body may include a silicone material. The reservoir may be pressurized such that activation of the spool to the inflation mode causes at least a portion of the fluid to transfer from the reservoir to the inflatable member through the pump assembly without operating the pump. When the spool is in the inflation mode, the pump may be configured to be depressed causing the fluid to transfer from the reservoir to the inflatable member through the pump assembly. Activation of the spool to the deflation mode may cause at least a portion of the fluid to transfer from the inflatable member to the reservoir through the pump assembly without operating the pump. The inflatable member may include at least two cylinders. The reservoir may include a biased member configured to pressurize the reservoir.

According to an aspect, an inflatable penile prosthesis includes an inflatable member, a reservoir configured to hold fluid, and a pump assembly configured to facilitate a transfer of the fluid from the reservoir to the inflatable member when in an inflation mode, and facilitate the transfer of the fluid from the inflatable member to the reservoir when in a deflation mode. The pump assembly includes a pump defining a pump bulb and a valve body connector integrally formed with the pump bulb, where the valve body connector defines a cavity, a valve body that is at least partially disposed within the cavity of the valve body connector, where the valve body includes a first check valve and a second check valve, and a spool configured to move within a lumen of the valve body to switch between the inflation mode and the deflation mode.

According to various aspects, the inflatable penile prosthesis may include one or more of the above and/or below features (or any combination thereof). The spool may have a length longer than a width of the valve body such that a first end portion of the spool extends from one side of the valve body when in the inflation mode and a second end portion of the spool extends from the other side of the valve body when in the deflation mode. The valve body may include a first interior portion that defines a first fluid channel, a second fluid channel, and a third fluid channel that extend to the pump bulb. The valve body may include a second interior portion that define a fourth fluid channel for transferring the fluid to and from the reservoir and a fifth fluid channel for transferring the fluid to and from the inflatable member. The spool may be disposed between the first interior portion and the second interior portion. The spool may include an elongated cylindrical member defining a plurality of enlarged cylindrical portions and a plurality of reduced cylindrical portions.

According to an aspect, a method for operating an inflatable penile prosthesis includes moving a spool of a pump assembly to place the inflatable penile prosthesis in an inflation mode. The pump assembly further includes a pump, a 5-port valve body, a first check valve, and a second check valve. The method includes transferring fluid within a reservoir to the pump via the valve body and the first check valve, and transferring the fluid from the pump to an inflatable member via the valve body and the second check valve.

According to various aspects, the method may include one or more of the above and/or below features (or any combination thereof). The method may include moving the spool to place the inflatable penile prosthesis in a deflation mode, transferring the fluid within the inflatable member to the pump via the valve body, and transferring the fluid within the pump to the reservoir via the valve body and the second check valve. At least a portion of the fluid may be transferred from the reservoir to the inflatable member via the pump assembly without operating the pump.

BRIEF DESCRIPTION OF THE DRAWINGS

FIG. 4B illustrates a perspective of the pump assembly according to an aspect.

FIG. 4C illustrates another perspective of the pump assembly depicting an interior of a valve body according to an aspect.

DETAILED DESCRIPTION

Figure 1:
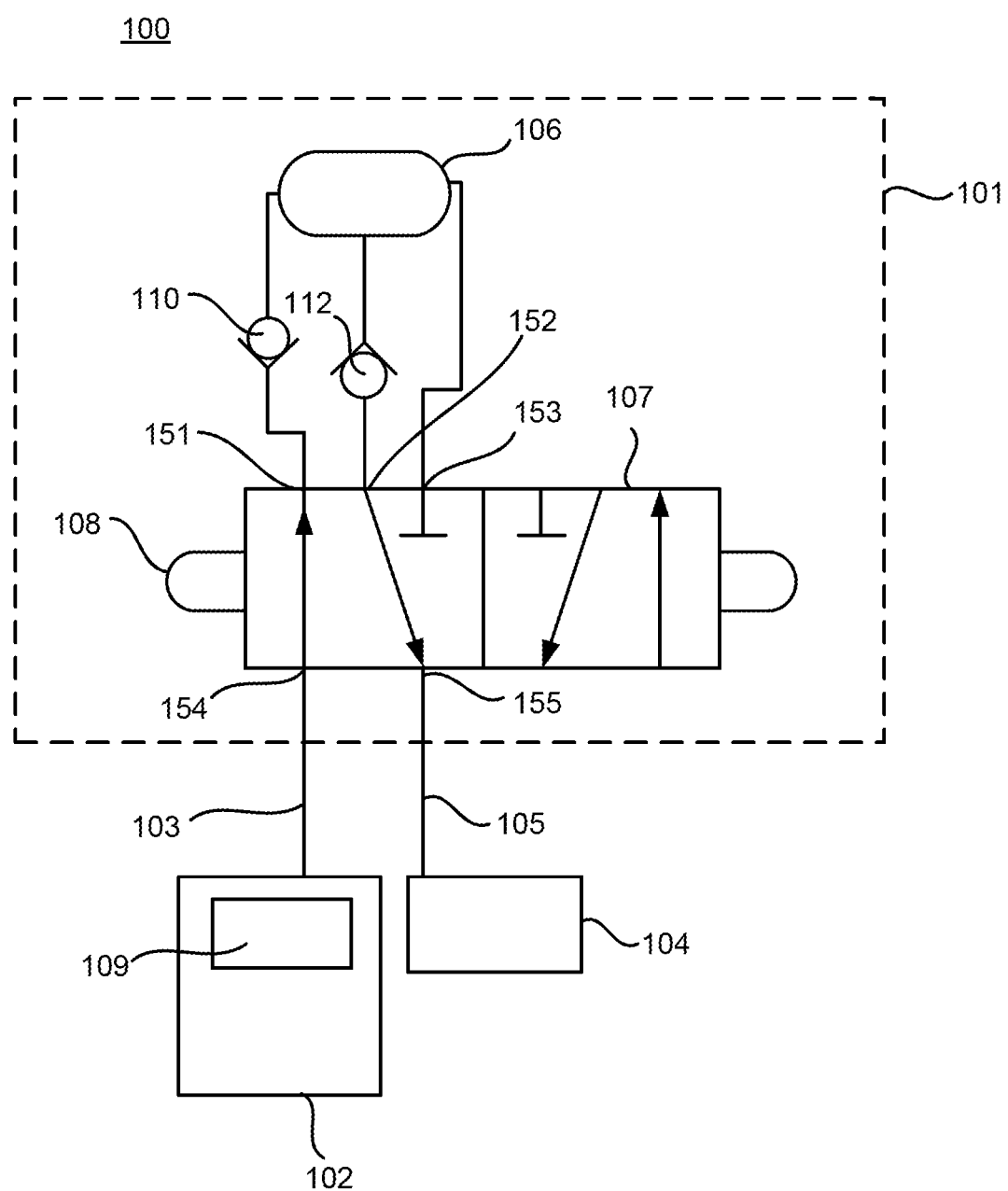
FIG. 1 schematically illustrates an inflatable penile prosthesis having a pump assembly according to an aspect.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are to medical devices (e.g., penile prostheses), methods of making medical devices, procedures for placing medical devices within a body of a patient, and methods for operating the medical devices. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The terms proximal and distal described in relation to various devices, apparatuses, and components as discussed in the subsequent text of the present disclosure are referred with a point of reference. The point of reference, as used in this description, is a perspective of a person who implants the inflatable penile prosthesis. The person may be a surgeon, a physician, a nurse, a doctor, a technician, and the like who may perform the implantation procedure. The term proximal refers to an area or portion that is closer or closest to the person during the implantation procedure. The term distal refers to an area or portion that is farther or farthest from the person.

The embodiments discussed herein may simplify the mechanism of selecting fluidic flow orientation, thereby increasing the number of patients that could successfully operate the erect/flaccid state control interface as well as increasing the reliability of the system. In some examples, the embodiments provide a next generation pump assembly to be used in a three-piece inflatable penile prosthesis system to reduce patient effort required to produce an erection suitable for penetration.

The embodiments may include an inflatable penile prosthesis having a pump assembly, an inflatable member, and a reservoir. The inflatable member may be implanted into the corpus cavernosae of a user, the reservoir may be implanted in the user's abdomen, and the pump assembly may be implanted in the scrotum. The pump assembly may include (1) a pump defining a pump bulb and a valve body connector, (2) a 5-port valve body (or 4-way valve body), and (3) a spool configured to move within the valve body and switch between an inflation position and a deflation position such that a user can operate the spool to place the inflatable penile prosthesis in either an inflation mode to transfer fluid from the reservoir to the inflatable member or an deflation mode to transfer the fluid from the inflatable member back to the reservoir. The pump assembly may also include (4) an inlet check valve, and (5) an outlet check valve.

The design of this inflatable penile prosthesis may reduce the number of components used for the pump assembly, thereby simplifying the overall design and functionality of the device, which may improve pump performance. In some examples, the total number of components may be reduced to five components. For instance, one of the benefits of the reduced part count is to isolate pump performance variability by having fewer components that affect the overall functionality of the pump assembly. Furthermore, in some examples, metal is not used for any of the components of the pump assembly. In some examples, the spool may be molded from a low friction coefficient and bio-compatible plastic. In some examples, the pump, the valve body, and the first and second check valves may be constructed from a molded medium durometer silicone. Removing metal from the overall design may make the pump assembly MM compatible (MR Safe Rating), which may reduce or eliminate against risks associated with long term oxidation of any metallic surfaces that could pose a potential risk to the body or the pump performance over its full life cycle.

Also, the embodiments may simplify the implantation procedure by providing operating room power pump priming feature. For instance, in some examples, the maximum back pressure rating on the first and second check valves is approximately 160 psi, which may indicate that there is little to no risk associated with damaging the pump from inflating the pump in the wrong position. This would allow for the prepping surgeon or operating room nurse to prime the pump more simply and effectively without having to remove it from the packaging or having to place it in an open basis full of saline solution to manually prime the pump (less preparation fatigue). In some examples, the pump assembly may provide a full "lockout" feature of the deflate position. For instance, while the spool is in the deflate position, fluid is allowed to drain back from the inflatable member (e.g., inflatable cylinders) to the reservoir through the second check valve, but fluid is prevented from flowing back the other way due to the maximum back pressure rating being relatively high. As such, the potential risk with spontaneous inflation may be negated considering the 160 psi back pressure rating of the second check valve.

In some examples, the reservoir may be pressurized. During use, the user may place the spool of the pump assembly to the inflation position which may cause fluid to be automatically transferred from the reservoir through the pump assembly to the inflatable member (e.g., due to pressure within the reservoir being greater than the inflatable member), which may result in the at least partial inflation of the inflatable member. Then, the user may actuate the pump bulb of the pump assembly to further transfer the fluid from the reservoir to the inflatable member, to provide the desired penis rigidity for a normal erection. In some examples, the automatic transfer to fluid to the inflatable member may cause a reduction in the amount of pumps to provide the desired penis rigidity. Also, with added pressure to the reservoir, the pump bulb can be filled at a faster rate.

When the user desires to deflate the inflatable member, the user may manually operate the spool to the deflation position, and fluid may be automatically transferred from the inflatable member to the reservoir due to the difference in pressure between the inflatable member and the reservoir. Then, the user may squeeze the inflatable member to further deflate the inflatable member, which returns the penis to a flaccid state.

FIG. 1 schematically illustrates an inflatable penile prosthesis 100 according to an aspect. The inflatable penile prosthesis 100 may include a reservoir 102, an inflatable member 104, and a pump assembly 101 configured to transfer fluid between the reservoir 102 and the inflatable member 104. In some examples, the inflatable member 104 may be implanted into the corpus cavernosae of the user, the reservoir 102 may be implanted in the abdomen or pelvic cavity of the user (e.g., the reservoir 102 may be implanted in the lower portion of the user's abdominal cavity or the upper portion of the user's pelvic cavity), and the pump assembly 101 may be implanted in the scrotum of the user.

The inflatable member 104 may include one or more elongate members capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. In some examples, each cylinder may include a cylindrical silicone rubber body or sleeve which, owing to its resiliency, is expandable circumferentially and also longitudinally. The volumetric capacity of the inflatable member 104 may depend on the size of the cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member. Further details of the cylinders are further explained with reference to FIGS. 2-3.

The reservoir 102 may include a container having an internal chamber configured to hold fluid that is used to inflate the inflatable member 104. The volumetric capacity of the reservoir 102 may vary depending on the size of the inflatable penile prosthesis 100. In some examples, the volumetric capacity of the reservoir 102 may be 40-50 cubic centimeters. In some examples, the reservoir 102 is constructed from the same material as the inflatable member 104. In other examples, the reservoir 102 is constructed from a different material than the inflatable member 104.

In some examples, the reservoir 102 may be pressurized. In some examples, the reservoir 102 is pressurized less than or equal to a pressurized threshold. In some examples, the reservoir 102 is pressurized to be equal to or less than diastolic pressure in order to ensure that the reservoir 102 is not over pressurized. In some examples, the pressurized threshold is 70 mm/Hg. In some examples, the pressurized threshold is greater than 70 mm/Hg. In other examples, the pressurized threshold is less than 70 mm/Hg. In some examples, the reservoir 102 includes a pressure regulating balloon. In other examples, the reservoir 102 is not pressurized (e.g., static). In some examples, reservoir 102 may include a single container configured to hold the fluid, which may or may not be pressurized. In some examples, the reservoir 102 includes a primary container (or primary chamber) and a secondary container (or secondary chamber), where the primary container/chamber may hold the fluid that is transferred to the inflatable member 104, and the secondary container/chamber may include gas or secondary fluid that is used to pressurize the fluid in the primary container/chamber.

In some examples, the reservoir 102 may include a biasing member 109 configured to pressurize the fluid in the reservoir 102. For example, upon injection of fluid into the reservoir 102, the biasing member 109 may provide a force on the fluid, thereby pressurizing the reservoir 102. The biasing member 109 may be biased to an original size or position, and the biasing member 109 may expand to a different size or position when the fluid is injected into the reservoir 102 and/or the biasing member 109, thereby creating a pressurized reservoir 102. In some examples, the biasing member 109 may include a spring or a spring-loaded assembly that biases the reservoir 102 to a particular size or position. In some examples, the biasing member 109 may be an expandable balloon inside a more rigid container of the reservoir 102. For instance, the expandable balloon may be biased to a smaller size when it is not filled with fluid. Then, upon injection of the fluid into the expandable balloon, the expandable balloon may expand and pressurize the fluid contained therein. In some examples, the biasing member 109 may be a biased diaphragm, which may be a membrane, flap, or other structure contained within the reservoir 102 that may separate one area of the reservoir 102 from another area of the reservoir 102. The diaphragm may be biased to an original position. Upon injection of the fluid into the reservoir 102, the diaphragm may flex, expand, or move to account for the increased fluid such that the fluid can be pressurized within the reservoir 102. In other examples, the reservoir 102 may be constructed from a substantially elastic walled abdominal conforming member. For example, the reservoir 102 may be located in in the abdomen within the space of retzius (retropubic space) or other sub-muscular locations, and the reservoir 102 may pre-charged or pressurized (to at least two or three psi) ahead of the desired moment of transformation of the penis from flaccid to erect due to the substantially elastic walled abdominal conforming member.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 may be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 may include a single or multiple tube members for transferring the fluid between the pump assembly 101 and the inflatable member 104. In some examples, the first conduit connector 103 and the second conduit connector 105 may include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 may include a pump 106, and a valve body 107 defining at least three ports (e.g., first port 151, second port 152, and third port 153) operatively coupled to the pump 106 and at least two ports (e.g., fourth port 154, fifth port 155) operatively coupled to the inflation member 104 and the reservoir 102. The pump assembly 101 may include a first check valve 110, a second check valve 112, and a spool 108. In some examples, metal is not used for any of the components of the pump assembly 101. In some examples, each component of the pump assembly 101 may include a polymer material. In some examples, each component of the pump assembly 101 includes a polymer material of the same type. In some examples, at least one component of the pump assembly 101 may include a non-metal material that is different from other components of the pump assembly 101. In some examples, the spool 108 may be molded from a low friction coefficient and bio-compatible plastic. In some examples, the pump 106, the valve body 107, and the first and second check valves 110, 112 may include a silicone material. In some examples, the pump 106, the valve body 107, and the first and second check valves 110, 112 may be constructed from a molded silicone material having a medium durometer value. Removing metal from the overall design may provide make the pump assembly 101 MRI compatible (MR Safe Rating), which may reduce or eliminate against risks associated with long term oxidation of any metallic surfaces that could pose a potential risk to the body or the pump performance over its full life cycle.

The pump 106 may be squeezed or depressed by the user in order to facilitate the transfer of fluid from the reservoir 102 to the inflatable member 104. For example, in the inflation mode, while the user is operating the pump 106, the pump 106 may receive the fluid from the reservoir 102, and then output the fluid to the inflatable member 104. When the user switches to the deflation mode, at least some of the fluid can automatically be transferred back to the reservoir 102 (due to the difference in pressure from the inflatable member 104 to the reservoir 102). Then, the user may squeeze the inflatable member 104 to facilitate the further transfer of fluid through the pump 106 to the reservoir 102.

In some examples, the pump 106 may include a flexible member defining a cavity. In some examples, the pump 106 may define a pump shell having a flexible bulb and a valve body connector, where the valve body connector is designed to fit at least partially over the valve body 107, as shown in FIGS. 4A-F. In some examples, the pump 106 may include a squeeze pump. In some examples, the pump 106 may include a portion that is round or substantially round. In some examples, the pump 106 may include ribbing or dimples to aid the user in gripping the pump 106. The pump 106 may use suction and pressure to move the fluid in and out of the cavity of the pump 106 in the inflation mode. For example, the user may depress or squeeze the pump 106 to expel the fluid out of the cavity, and, when the flexible member returns to its original shape, the resulting suction pushes the fluid into the cavity of the pump 106. In some examples, the pump 106 may have a bulb spring rate that is designed to refill the pump 106 in a selected time frame. In some examples, the bulb spring rate (especially in the completely flattened state of the squeezed pump bulb) may be selectively enhanced to create a vacuum by the addition of a nitinol spring configured as a sphere that exerts opening force on the bulb walls. This spring could also be designed such that it does not substantially increase the compressive squeeze force required to expel fluid out of the bulb in the opened state through the use of hinge/buckle points.

The valve body 107 may include a structure that defines a plurality of ports configured to transfer to and from the pump 106. The ports defined by the valve body 107 may be openings and/or channels that are defined within the structure of the valve body 107. In some examples, the valve body 107 is a five-port valve enabling a 4-way valve. In some examples, valve body 107 may house or include the first check valve 110, the second check valve 112, and portions of the spool 108. In some examples, the valve body 107 may house these components within a rigid, dimensionally stable, and/or tightly toleranced insert surrounded by anatomically representative compliant materials enabling repeatable actuation of the internal valve components while maintaining patient comfort outwardly within the scrotum.

The valve body 107 may define a first port 151, a second port 152, and a third port 153 operatively coupled to the pump 106 such that three separate fluid channels extend between the valve body 107 and the pump 106. For example, the first port 151 may be operatively coupled to the pump 106 such that a first fluid channel extends between the valve body 107 and the pump 106. The second port 152 may be operatively coupled to the pump 106 such that a second fluid channel extends between the valve body 107 and the pump 106. The third port 153 may be operatively coupled to the pump 106 such that a third fluid channel extends between the valve body 107 and the pump 106. The first fluid channel, the second fluid channel, and the third fluid channel may be separate fluid channels that independently allow fluid from entering or exiting the pump 106.

The valve body 107 may define a fourth port 154 and a fifth port 155 operatively coupled to the reservoir 102 and the inflatable member 104 such that one fluid channel extends from the valve body 107 to the reservoir 102 and another fluid channel extends from the valve body 107 to the inflatable member 104. For example, the fourth port 154 may be operatively coupled to the reservoir 102 via the first conduit connector 103. The fifth port 155 may be operatively coupled to the reservoir 102 via the second conduit connector 105.

The first check valve 110 may be coupled to the pump 106. In some examples, the first check valve 110 is disposed within the first fluid channel that extends between the first port 151 and the pump 106. For example, the first check valve 110 may have an inlet that is operatively coupled to the first port 151 and an outlet that is operatively coupled to the pump 106. In some examples, the first check valve 110 may be an input check valve that permits fluid to flow into the pump 106. In some examples, the first check valve 110 is a pressure check valve. In some examples, the first check valve 110 has a maximum back pressure rating in a range of 140 psi-180 psi. In some examples, the first check valve 110 has a maximum back pressure rating of 160 psi. The first check valve 110 having one of these maximum back pressure ratings may reduce or eliminate the risk associated with damaging the pump 106 from inflating in the wrong position. The first check valve 110 may be coupled to the pump 106 such that fluid can flow into the pump 106 via the first check valve 110, and block the flow of fluid out of the pump 106 via the first check valve 110. In some examples, the first check valve 110 is a one-directional pressure check valve that only permits the passage of fluid in one direction. In other examples, the first check valve 110 includes a duckbill valve. For example, the duckbill valve may include a flattened (or substantially flattened) end portion at its outlet, and, when the pressure is greater than a threshold amount, the flattened end portion is configured to open to permit the fluid to pass. When the pressure is removed, the duckbill end may return to its flattened shape, preventing backflow. However, the first check valve 110 may include other types of valves such as a diaphragm check valve, a swing check valve, a tilting disc check valve, a stop-check valve, a lift-check valve, or an in-line check valve.

The second check valve 112 may be coupled to the pump 106. In some examples, the second check valve 112 is disposed within the second fluid channel that extends between the second port 152 and the pump 106. For example, the second check valve 112 may have an inlet that is operatively coupled to the pump 106 and an outlet that is operatively coupled to the second port 152. In some examples, the second check valve 112 may be an output check valve that permits fluid to flow out of the pump 106. In some examples, the second check valve 112 is a pressure check valve. In some examples, the second check valve 112 has a maximum back pressure rating in a range of 140 psi-180 psi. In some examples, the second check valve 112 has a maximum back pressure rating of 160 psi. The second check valve 112 having one of these maximum back pressure ratings may reduce or eliminate the risk associated with damaging the pump 106 from inflating in the wrong position. The second check valve 112 may be coupled to the pump 106 such that fluid can flow out of the pump 106 via the second check valve 112, and block the flow of fluid into the pump 106 via the second check valve 112. In some examples, the second check valve 112 is a one-directional pressure check valve that only permits the passage of fluid in one direction. In other examples, the second check valve 112 may include a duckbill valve, a diaphragm check valve, a swing check valve, a tilting disc check valve, a stop-check valve, a lift-check valve, or an in-line check valve.

In some examples, the first check valve 110 and the second check valve 112 may have the same type of valve. In other examples, the first check valve 110 may be a different type than the second check valve 112. In some examples, the first check valve 110 has a size that is smaller than the second check valve 112. In some examples, the pump assembly 101 may include one or more filters. For example, a filter may be disposed on the inlet of the first check valve 110 and/or the inlet of the second check valve 112. As shown in FIG. 1, the fluid channel that is defined between the third port 153 and the pump 106 is devoid of a check valve. Also, the fluid channel that exists between the fourth port 154 and the reservoir 102 and the fluid channel that exits between the fifth port 155 and the inflatable member 104 is devoid of any check valves.

The spool 108 may include an elongated member that extends (at least partially) within a lumen of the valve body 107. The spool 108 may be movable within the valve body 107 such that the spool 108 can move to the inflation position and the deflation position. In some examples, the length of the spool 108 may be longer than outer structure of the valve body 107 in at least one dimension (e.g., length, width, or thickness) such that a first end portion of the spool 108 extends from one side of the valve body 107 in the inflation position and a second end portion of the spool 108 extends from the other side of the valve body 107 in the deflation position.

In some examples, the spool 108 is an elongated cylindrical member. The spool 108 may include a plurality of enlarged portions and a plurality of reduced portions, where the plurality of enlarged portions block the transfer of fluid through the valve body 107 and the plurality of reduced portions permit the flow of fluid through the valve body 107. In some examples, the spool 108 may include a plurality of reduced cylindrical portions and a plurality of enlarged cylindrical portions that have a different diameter than the end portions of the spool 108. The user of the pump assembly 101 may switch a position of the spool 108 to either an inflation position or a deflation position. In other examples, the spool 108 may include more than two positions (e.g., a third position that corresponds to neither the inflation mode nor the deflation mode). In some examples, the spool 108 may allow the flow of fluid into different paths from the reservoir 102 and the inflatable member 104.

When within the inflation position (as shown in FIG. 1), the position of the spool 108 with respect to the valve body 107 permits the transfer of fluid from the reservoir 102 to the inflatable member 104. For example, when the spool 108 is within the inflation position, the fluid flows through the valve body 107 via four ports in the following fluid path: through the fourth port 154 to the first port 151 to the second port 152 and through the fifth port 155. The third port 153 is blocked by one of the enlarged portions of the spool 108. When within the deflation position, the position of the spool 108 with respect to the valve body 107 permits the transfer of fluid from the inflatable member 104 to the reservoir 102. For example, when the spool 108 is within the deflation position, the fluid flows through the valve body 107 via four ports in the following fluid path: through the fifth port 155 to the third port 153 to the second port 152 and through the fourth port 154). The first port 151 is blocked by one of the enlarged portions of the spool 108.

In some examples, if the reservoir 102 is at least partially pressurized, the fluid may automatically flow out of the reservoir 102 and into the inflatable member 104 without the user depressing or squeezing the pump 106 until the pressure is at least partially equalized between the reservoir 102 and the inflatable member 104.

In some examples, the user may operate the pump 106 to inflate the inflatable member 104. For example, the user may repeatedly depress or squeeze the pump 106 until the desired rigidity is achieved. With respect to a single pump cycle, initially, both of the first check valve 110 and the second check valve 112 are closed. For example, both the first check valve 110 and the second check valve 112 may be closed at pressure equilibrium. Then, the user depresses or squeezes the pump 106 until the pressure exceeds the pressure threshold of the second check valve 112, which may cause the fluid in the pump 106 to transfer to the inflatable member 104 via the second check valve 112, the valve body 107, and the second conduit connector 105. For example, squeezing the pump 106 may open the second check valve 112 (where the first check valve 110 is closed) until no volume in the pump 106 can overcome the outlet pressure. The pump 106 may then return to its original form, which provides a suction force causing the first check valve 110 to open (where the second check valve 112 is closed) such that fluid is transferred from the reservoir 102 to the pump 106 via the first conduit connector 103, the valve body 107, and the first check valve 110. For example, release of the user's finger on the pump 106 may create a vacuum in the pump 106 and the first check valve 110 may open. The flow from the reservoir 102 fills the pump 106 (or at least partially fills the pump 106) until the pump's pressure is substantially equal to the reservoir's pressure. After the pump 106 returns to its original form, the first check valve 110 and the second check valve 112 may return to their closed states. This pump cycle is repeated until the desired rigidity in the inflatable member 104 is achieved.

Then, when the user wants to deflate the inflatable member 104, the user moves the spool 108 to the deflation position causing one of the ports to be opened (e.g., the third port 153 that was closed in the inflation position is thereby opened), and one of the ports to be closed (e.g., the first port 151 that was opened in the inflation position is thereby closed). Furthermore, when the user moves the spool 108 to the deflation position, the fluid flow exiting the second port is changed (e.g., the spool 108 directs the fluid flow from the second port 152 to the fourth port 154 in the deflation position as opposed from the second port 152 to the fifth port 155 when the spool 108 was in the inflation position). Therefore, when the spool 108 is in the deflation position, one of the reduced portions of the spool 108 allows the fluid to be transferred through the valve body 107 from the fifth port 115 to the third port 153, which enters the pump 106 via the third fluid channel (e.g., the one that is devoid of a check valve). In some examples, in the second deflation position, the fluid may automatically flow out of the inflatable member 104 and into the reservoir 102 without the user depressing or squeezing the pump 106 until the pressure is at least partially equalized between the reservoir 102 and the inflatable member 104. Then, the user may squeeze the inflatable member 104 to further facilitate the transfer to fluid from the inflatable member 104 to the reservoir 102. In some examples, the user may operate the pump 106 to deflate the inflatable member 104 to return the penis to a flaccid state. For example, the user may repeatedly depress or squeeze the pump 106 until the inflatable member 104 is sufficiently deflated.

As indicated above, the design of this inflatable penile prosthesis 100 may reduce the number of components used for the pump assembly 101, thereby simplifying the overall design and functionality of the device, which may improve pump performance. In some examples, the total number of components may be reduced to five components. For instance, one of the benefits of the reduced part count is to isolate pump performance variability by having fewer components that affect the overall functionality of the pump assembly 101.

Figure 2:
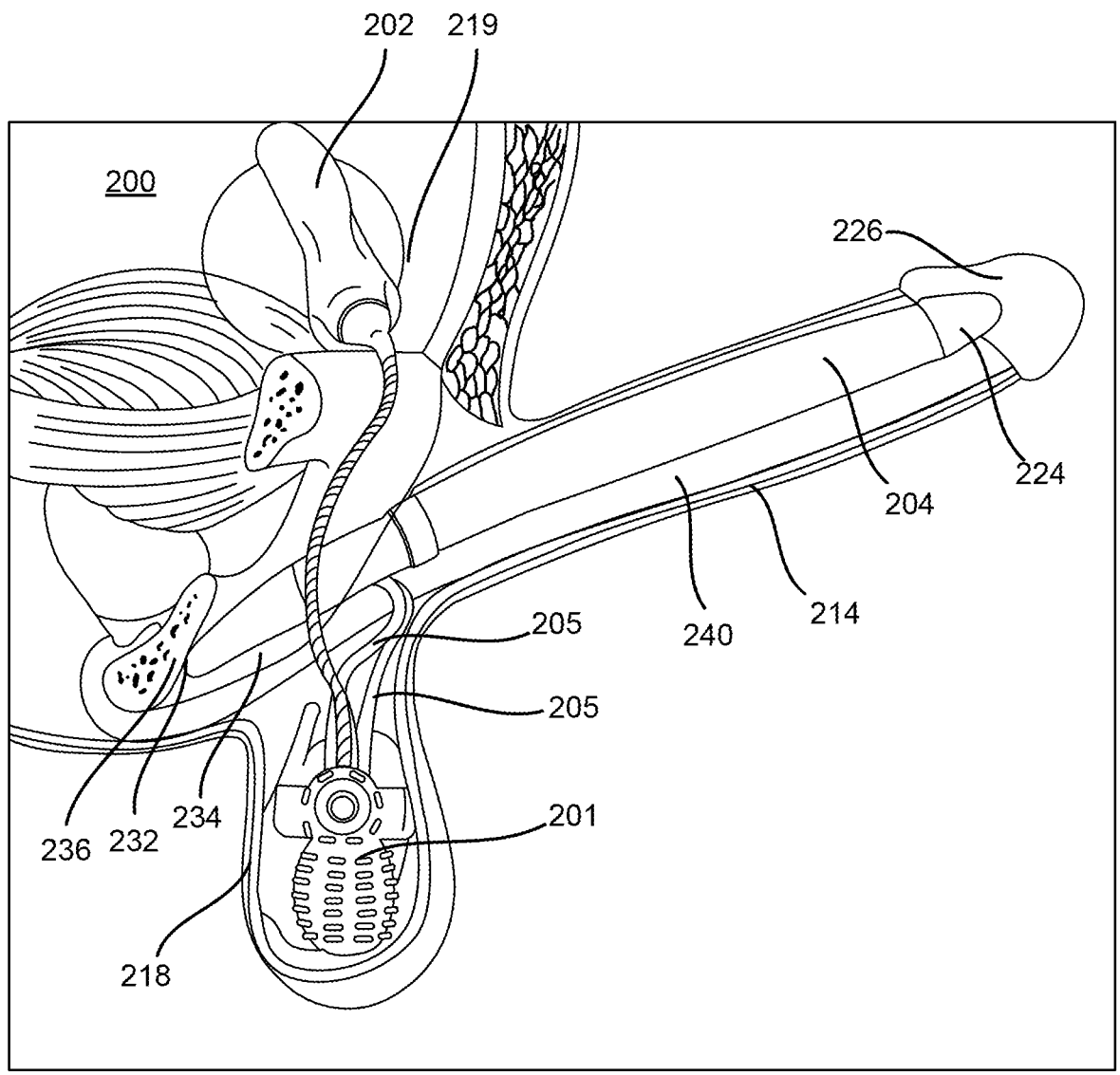
FIG. 2 illustrates an inflatable penile prosthesis implanted within a user according to an aspect.
Figure 3:
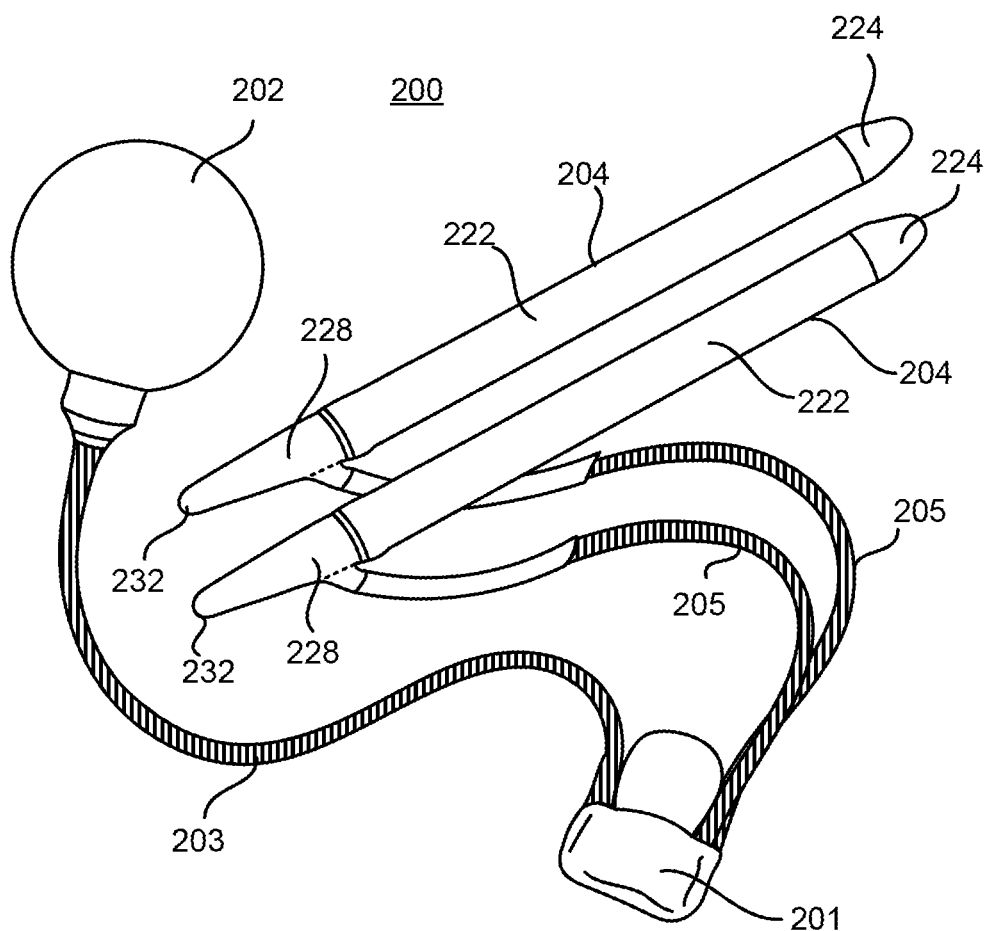
FIG. 3 illustrates an inflatable penile prosthesis according to another aspect.

FIG. 2 illustrates an inflatable penile prosthesis 200 implanted within a user according to an aspect. In some examples, the inflatable penile prosthesis 200 may be the inflatable penile prosthesis 100 of FIG. 1 or include any (or any combination) of the features discussed herein with respect to any of the figures. FIG. 3 illustrates the inflatable penile prosthesis 200 having a pair of cylinders 204.

Referring to FIGS. 2-3, the inflatable penile prosthesis 200 may include a pair of cylinders 204, and the pair of cylinders 204 are implanted in a penis 214. For example, one of the cylinders 204 may be disposed on one side of the penis 214. The other cylinder 204 (not shown in FIG. 2) of the pair of cylinders may be disposed on the other side of the penis 214. The cylinder 204 may include a distal end portion 224, an inflation chamber 222, and a proximal end portion 228 having a rear tip 232.

The inflatable penile prosthesis 200 may include a pump assembly 201, which may be implanted into the patient's scrotum 218. The pump assembly 201 may include any of the features discussed with reference to the reversible flow pump assembly of any of the figures. A pair of conduit connectors 205 may attach the pump assembly 201 to the pair of cylinders 204 such that the pump assembly 201 is in fluid communication with the pair of cylinders 204. Also, the pump assembly 201 may be in fluid communication with a reservoir 202 via a conduit connector 203, where the reservoir 202 that may be implanted into the user's abdomen 219. The inflation chamber 222 of the cylinder 204 may be disposed within the penis 214. The distal end portion 224 of the cylinder 204 may be at least partially disposed within the crown portion 226 of the penis 214. The proximal end portion 228 may be implanted into the patient's pubic region 234 with the rear tip 232 proximate the pubic bone 236.

In order to implant the cylinder 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area (proximal corpora cavernosae) to prepare the patient to receive the proximal end portion 228. The surgeon may measure the length of the proximal and distal corpora cavernosae from the incision and the dilated region of the pubic area to determine an appropriate size of the cylinder 204 to implant.

After the patient is prepared, the inflatable penile prosthesis 200 is implanted into the patient. The distal tip of the distal end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown of the penis 214. The surgeon tugs on the suture to pull the cylinder 204 into the corpus cavernosum. This is done for each cylinder of the pair of cylinders 204. Once the inflation chamber 222 is in place, the surgeon may remove the suture from the distal tip. The surgeon then inserts the proximal end portion 228. The surgeon inserts the rear end of the cylinder 204 into the incision and forces the proximal end portion 228 toward the pubic bone 236 until each cylinder 204 is in place.

FIGS. 4A-4F illustrate various perspectives of a pump assembly 401 according to an aspect. The pump assembly 401 may be an embodiment of the pump assembly 101/201 of FIGS. 1-3, and may include one or more features (or any combination thereof) previously explained with reference to these figures.

Figure 4A:
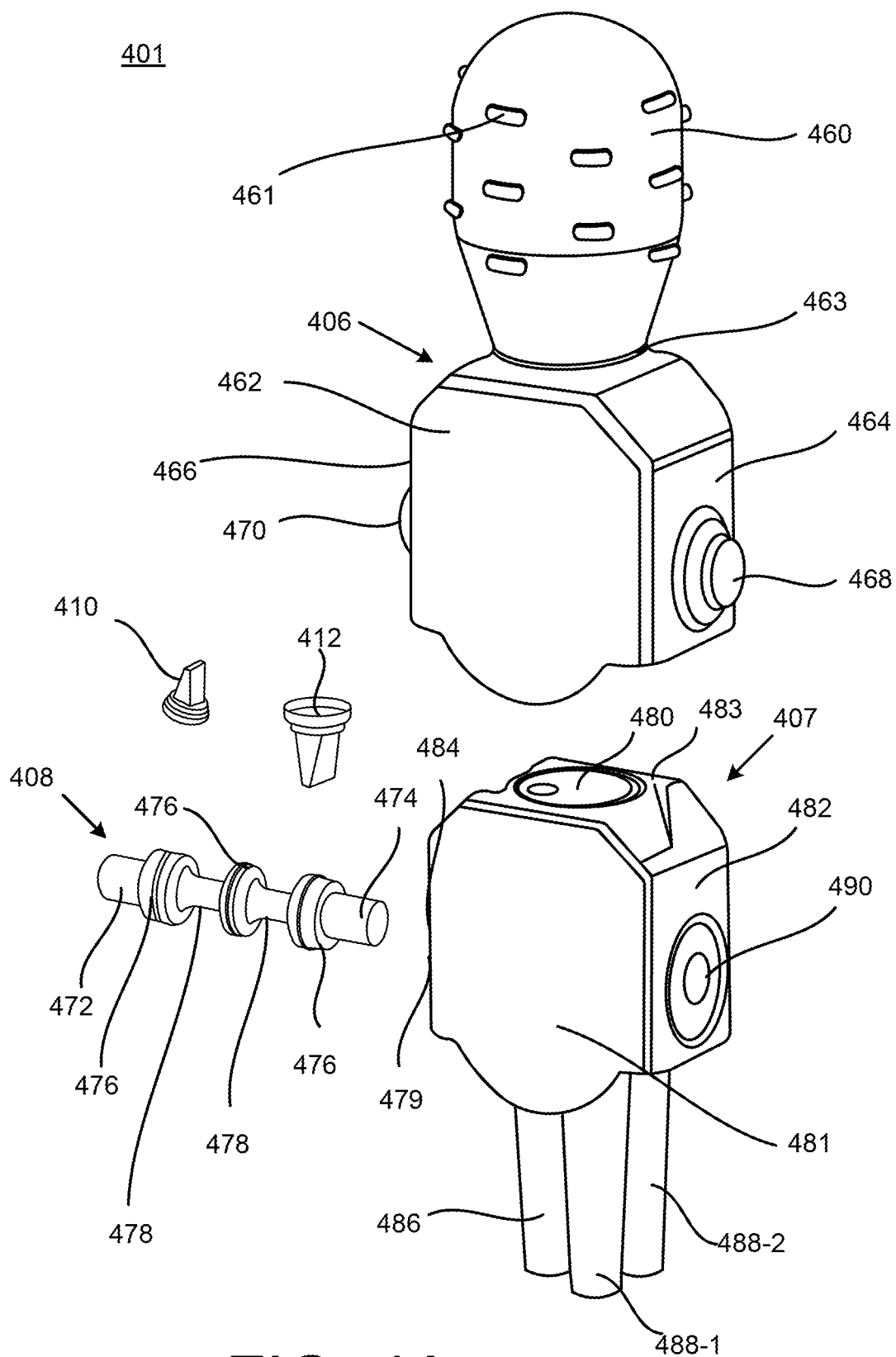
FIG. 4A illustrates unassembled components of a pump assembly according to an aspect.
Figure 4D:
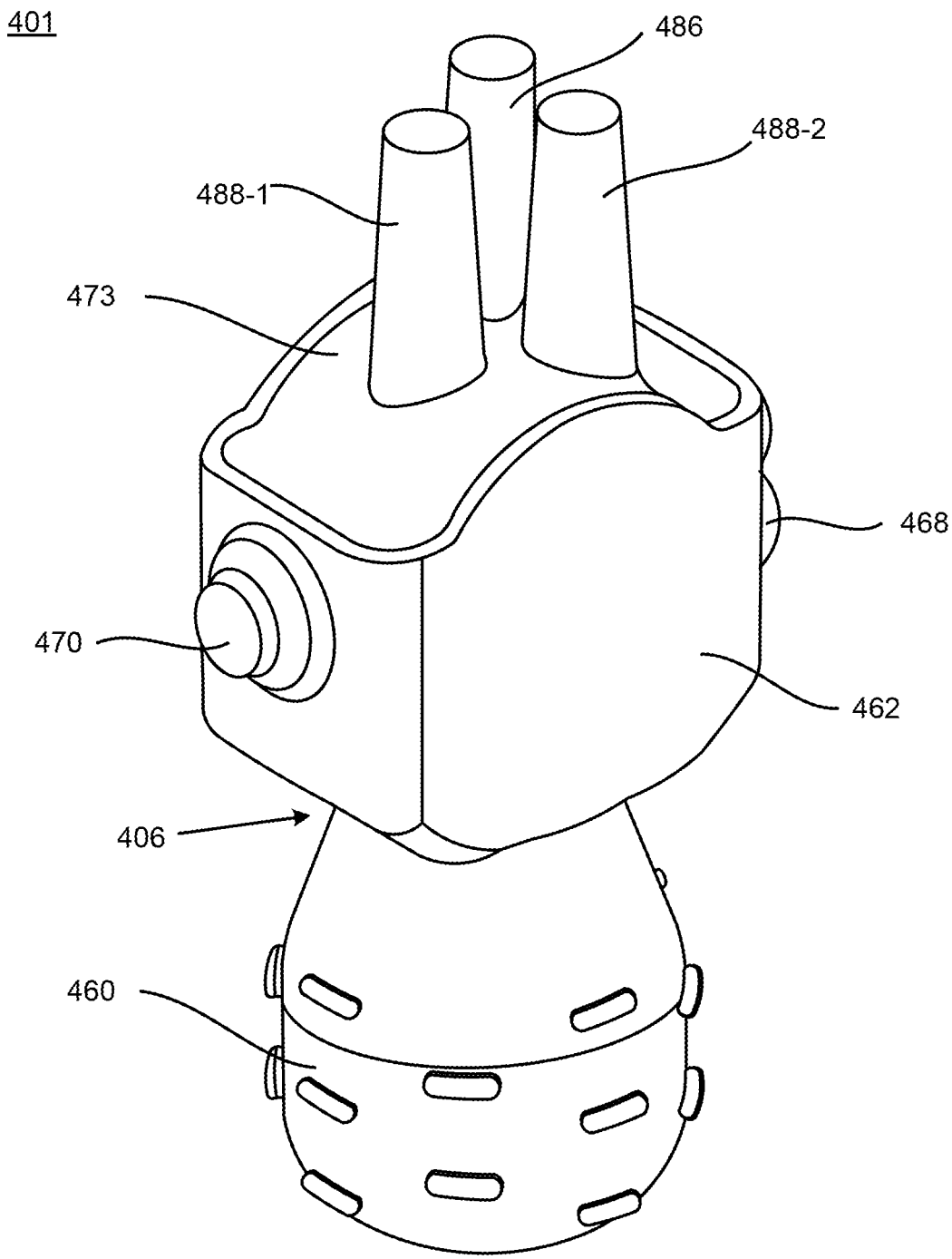
FIG. 4D illustrates another perspective of the pump assembly according to an aspect.
Figure 4E:
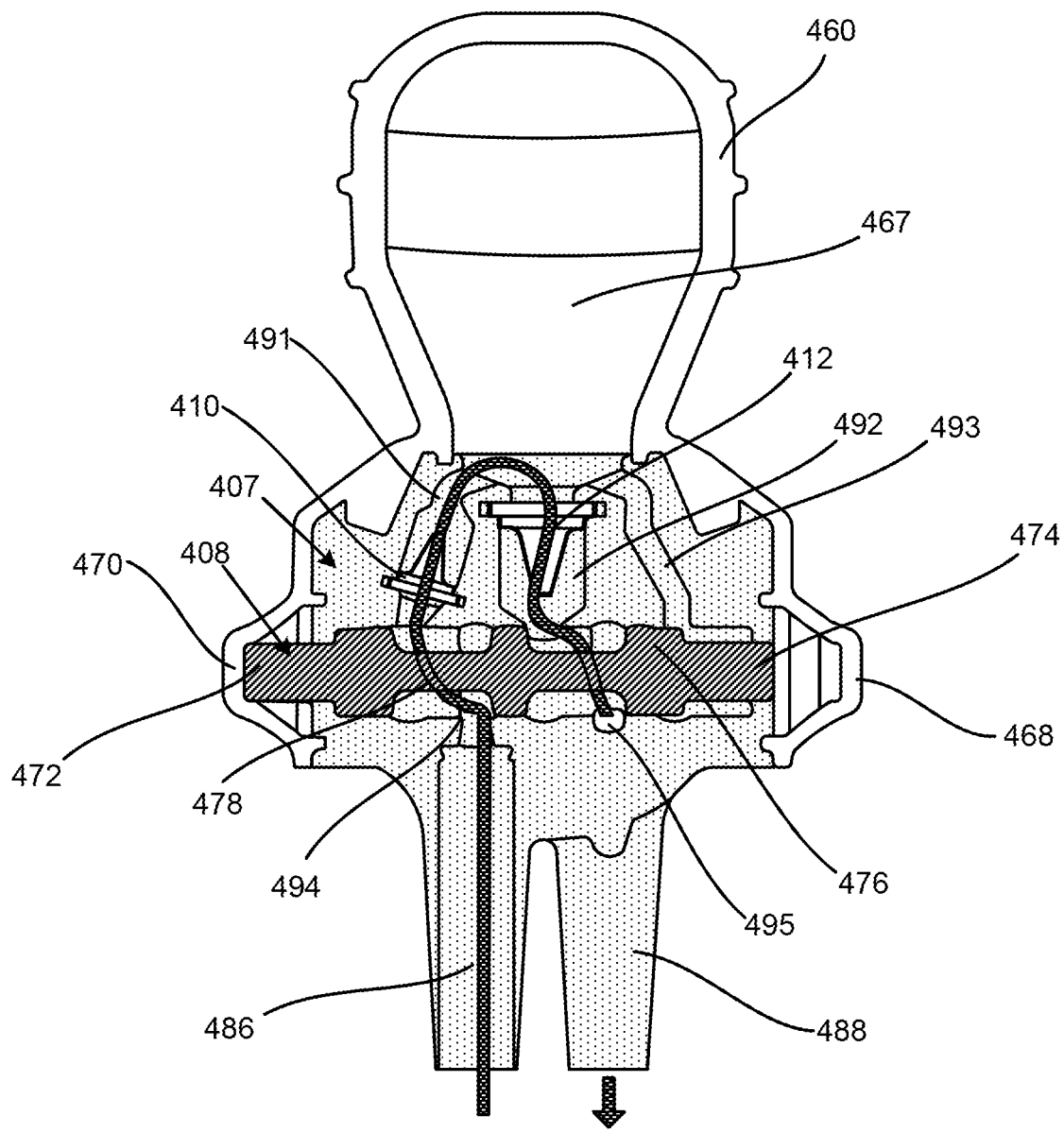
FIG. 4E illustrates another perspective of the pump assembly depicting the inflation fluid flow through the valve body according to an aspect.
Figure 4F:
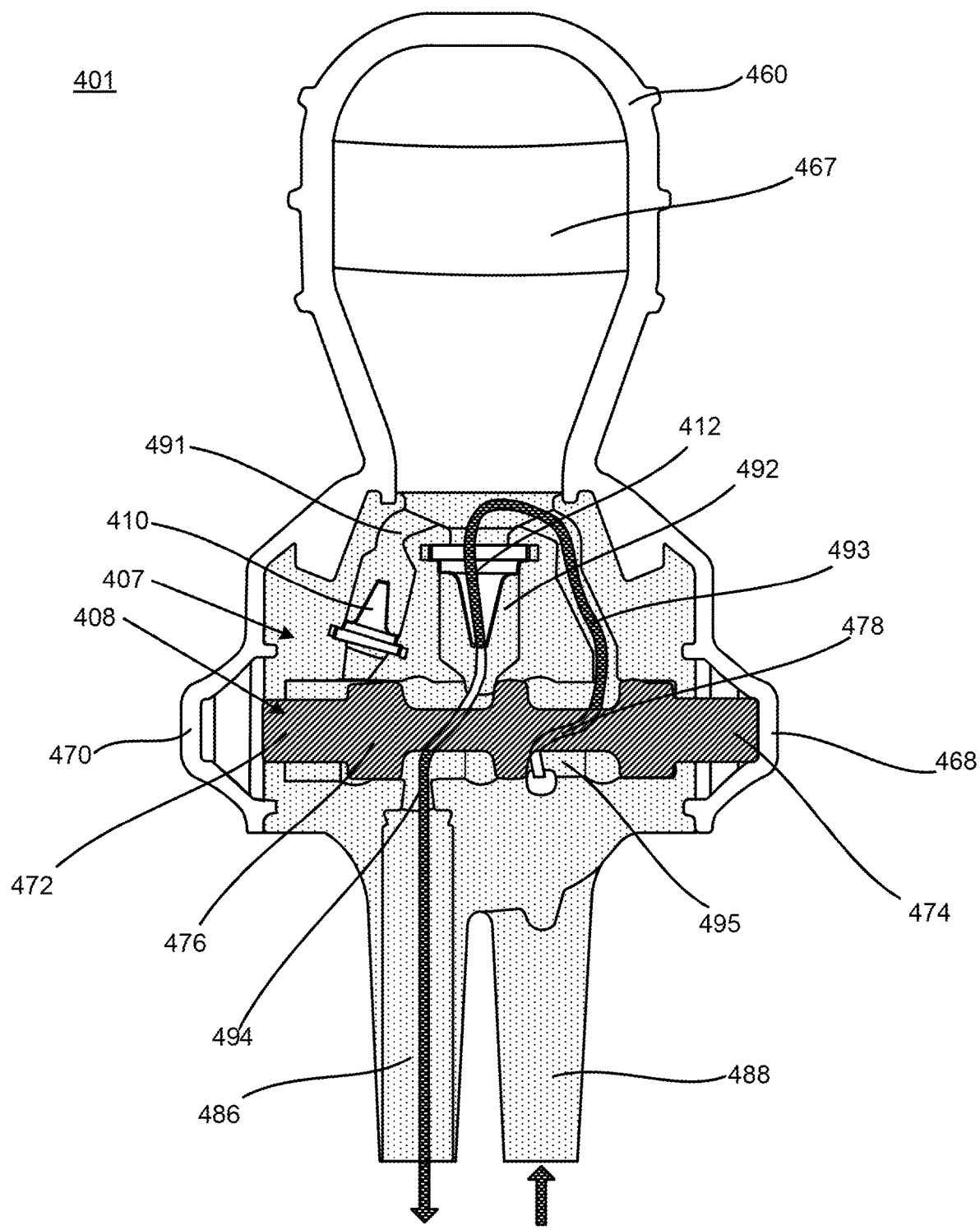
FIG. 4F illustrates another perspective of the pump assembly depicting the deflation fluid flow through the valve body according to an aspect.

FIG. 4A illustrates unassembled components of the pump assembly 401 according to an aspect. FIG. 4B illustrates a perspective of the pump assembly 401 according to an aspect. FIG. 4C illustrates another perspective of the pump assembly 401 depicting an interior of the valve body 407 according to an aspect. FIG. 4D illustrates another perspective of the pump assembly 401 according to an aspect. FIG. 4E illustrates another perspective of the pump assembly 401 depicting the inflation fluid flow through the valve body 407 according to an aspect. FIG. 4F illustrates another perspective of the pump assembly 401 depicting the deflation fluid flow through the valve body 407 according to an aspect.

The pump assembly 401 may include a pump 406, a first check valve 410, a second check valve 412, a spool 408, and a valve body 407. In some examples, the pump 406, the first check valve 410, the second check valve 412, the spool 408, and the valve body 407 may be devoid of a metal or metal-based material. In some examples, each of the pump 406, the first check valve 410, the second check valve 412, the spool 408, and the valve body 407 may include a polymer material (or constructed entirely of a polymer material). In some examples, the spool 408 may be molded from a low friction coefficient and a bio-compatible plastic. In some examples, the pump 406, the valve body 407, and the first and second check valves 410, 412 may include a silicone material. In some examples, the pump 406, the valve body 407, and the first and second check valves 410, 412 may be constructed from a molded silicone material having a medium durometer value. Removing metal from the overall design may make the pump assembly 401 MRI compatible (MR Safe Rating), which may reduce or eliminate against risks associated with long term oxidation of any metallic surfaces that could pose a potential risk to the body or the pump performance over its full life cycle.

The pump 406 may include a pump bulb 460 and a valve body connector 462. The pump bulb 460 may be a flexible member defining a cavity 467. The pump bulb 460 may be a squeeze pump. In some examples, the pump bulb 460 may include ribbing or dimples 461 to aid the user in gripping the pump bulb 460. The pump bulb 460 may use suction and pressure to move the fluid in and out of the cavity 467 of the pump bulb 460 in the inflation position. For example, the user may depress or squeeze the pump bulb 460 to expel the fluid out of the cavity 467, and, when the flexible member returns to its original shape, the resulting suction pushes the fluid into the cavity 467 of the pump bulb 460. In some examples, the pump bulb 460 may have a bulb spring rate that is designed to refill the pump bulb 460 in a selected time frame. In some examples, the bulb spring rate (especially in the completely flattened state of the squeezed pump bulb) may be selectively enhanced to create a vacuum by the addition of a nitinol spring configured as a sphere that exerts opening force on the bulb walls. This spring could also be designed such that it does not substantially increase the compressive squeeze force required to expel fluid out of the bulb in the opened state through the use of hinge/buckle points.

The valve body connector 462 may extend from a base 463 of the pump bulb 460. The valve body connector 462 may define a cavity that receives a main portion 481 of the valve body 407. For example, the valve body connector 462 may fit over the main portion 481 of the valve body 407 in order to couple the pump 406 to the valve body 407. In some examples, the main portion 481 of the valve body 407 may be coupled within the valve body connector 462 based on an interference fit. In other examples, the main portion 481 of the valve body 407 may be coupled within the valve body connector 462 using an attachment mechanism such as an adhesive. Generally, the valve body connector 462 may have a shape that corresponds to the main portion 481 of the valve body 407. The valve body connector 462 may include a first side portion 464 and a second side portion 466 opposite to the first side portion 464. The first side portion 464 may include a first flexible member 468. The second side portion 466 may include a second flexible member 470. Based on user pressure applied to the first flexible member 468 and the second flexible member 470, the first flexible member 468 and the second flexible member 470 may flex inwardly in order to move the spool 408.

The valve body connector 462 and the pump bulb 460 may be integrally formed such that the valve body connector 462 and the pump bulb 460 are a single plastic component (also referred to as a pump shell) defining a continuous cavity. In other examples, the valve body connector 462 and the pump bulb 460 are separately formed and coupled together using an attachment mechanism.

The main portion 481 of the valve body 407 may have a structure that generally corresponds to the structure of the valve body connector 462. However, the main portion 481 of the valve body 407 may have a slightly smaller shape than the valve body connector 462 such that the main portion 481 of the valve body 407 can fit inside the valve body connector 462. The interior of the main portion 481 of the valve body 407 is explained at a later point in the disclosure. The valve body 407 may include a reservoir extender 486 that transfers fluid to and from the reservoir 102 and one or more inflatable member extenders 488-1, 488-2 that transfers fluid to and from the inflatable member 104. For instance, in some examples, the inflatable member 104 may include a pair of cylinders, and, each of the inflatable member extenders 488-1, 488-2 may be operatively coupled to a different cylinder. In other examples, the pump assembly 401 includes only one inflatable member extender (e.g., 488-1 or 488-2) that is operatively coupled to the pair of cylinders. In some examples, the reservoir extender 486 and the inflatable member extenders 488-1, 488-2 may extend from a bottom portion 473 (opposite to the opening 480). In some examples, the reservoir extender 486 and the inflatable member extenders 488-1, 488-2 may be generally tubular members defining cavities. The reservoir extender 486 may be coupled to the first conduit member 103/203 of FIGS. 1-3, and the inflatable member extenders 488-1, 488-2 may be coupled to the second conduit member 105/205 of FIGS. 1-3.

The valve body 407 may define an opening 480 on a top portion 483 of the valve body 407. When the valve body connector 462 is disposed over the main portion 481 of the valve body 407, the opening 480 of the valve body 407 may be disposed proximate to the base 463 of the pump bulb 460. The opening 480 may permit fluid to be transferred between the valve body 407 and the pump bulb 460. The valve body 407 may define a first side portion 482 and a second side portion 484 that is opposite to the first side portion 482. The first side portion 482 may define a first side opening 490.

The second side portion 484 may define a second side opening 479. The valve body 407 may define a lumen that extends between the first side opening 490 and the second side opening 479. The first check valve 410 and the second check valve 412 may be coupled within the structure of the valve body 407. For example, the first check valve 410 and the second check valve 412 may be inserted into the valve body 407 via the opening 480, and coupled within a different fluid channel using an adhesive.

The spool 408 may be an elongated member having a first end portion 472 and a second end portion 474. In some examples, the spool 408 may be a cylindrical member having a diameter. The spool 408 may include enlarged portions 476 and reduced portions 478. In some examples, the enlarged portions 476 are cylindrical portions, and the reduced portions 478 are cylindrical portions. However, the enlarged portions 476 and the reduced portions 478 may include other types of shapes such as having a curved portion, bent portion, and/or linear portions. In some examples, adjacent enlarged portions 476 may be spaced apart by a single reduced portion 478. In some examples, the first end portion 472 and the second end portion 474 have a first diameter, the enlarged portions 476 have a second diameter, and the reduced portions 478 have a third diameter. The second diameter may be greater than the first diameter and the third diameter. The first diameter may be greater than the third diameter but less than the second diameter. The third diameter may be smaller than both the first diameter and the second diameter.

The spool 408 may be inserted into the valve body 407 such that the spool 408 extends between the first side opening 490 and the second side opening 479. In some examples, the spool 408 may have a length larger than a width of the valve body 407 (e.g., the width being defined by the distance between the first side portion 482 and the second side portion 484). In some examples, in the inflation position, the first end portion 472 of the spool 408 protrudes from the second side portion 484 of the valve body 407, and the second end portion 474 of the spool 408 is either flush with the first side portion 482 or is contained within the valve body 407. In some examples, in the deflation position, the second end portion 474 of the spool 408 protrudes from the first side portion 482, and the first end portion 472 of the spool 408 is either flush with the second side portion 484 or is contained is contained within the valve body 407. Therefore, the user may switch between the inflation position and the deflation position by moving the spool 408 within the lumen defined between the first side opening 490 and the second side opening 479. For example, when the pump assembly is assembled (e.g., when the spool 408 is inserted into the lumen extending from the first side opening 490 to the second side opening 479, and the valve body connector 462 is fitted over the main portion 481 of the valve body 407), the user may depress either the first flexible member 468 or the second flexible member 470 to move the spool 408 between the inflation position and the deflation position.

Referring to FIG. 4C, the valve body 407 may include an upper interior portion 498 and a lower interior portion 499. The spool 408 may be disposed between the upper interior portion 498 and the lower interior portion 499. The upper interior portion 489 may define three separate fluid channels 491, 492, 493 that extend to the pump bulb 460. For example, the upper interior portion 489 may define a first fluid channel 491, a second fluid channel 492, and a third fluid channel 493. The first fluid channel 491, the second fluid channel 492, and the third fluid channel 493 may be separate and independently fluid paths in each fluid can flow into and out of the valve body 407 and/or the pump bulb 460. In some examples, the second fluid channel 492 is larger than the first fluid channel 491 and the third fluid channel 493. The lower interior portion 499 may define a fourth fluid channel 494 that extends to the reservoir extender 486 and a fifth fluid channel 495 that extends to the inflatable member extender 488. In some examples, each of the fluid channels 491-495 may be slots, openings, or ports within the plastic molding of the valve body 407. In some examples, the valve body 407 is a five-port valve enabling a 4-way valve.

The first check valve 410 may be disposed within the first fluid channel 491. The first check valve 410 may be an input check valve that permits fluid to flow into the cavity 467 of the pump bulb 460. In some examples, the first check valve 410 is a pressure check valve. In some examples, the first check valve 410 has a maximum back pressure rating in a range of 140 psi-180 psi. In some examples, the first check valve 410 has a maximum back pressure rating of 160 psi. The first check valve 410 having one of these max back pressure ratings may reduce or eliminate the risk associated with damaging the pump bulb 460 from inflating in the wrong position. In other examples, the first check valve 410 includes a duckbill valve, a diaphragm check valve, a swing check valve, a tilting disc check valve, a stop-check valve, a lift-check valve, or an in-line check valve.

The second check valve 412 may be disposed within the second fluid channel 492 that extends to the pump bulb 460. The third fluid channel 493 may be devoid of a check valve. In some examples, the second check valve 412 may be an output check valve that permits fluid to flow out of the cavity 467 of the pump bulb 460. In some examples, the second check valve 412 is a pressure check valve. In some examples, the second check valve 412 has a maximum back pressure rating in a range of 140 psi-180 psi. In some examples, the second check valve 412 has a maximum back pressure rating of 160 psi. The second check valve 412 having one of these maximum back pressure ratings may reduce or eliminate the risk associated with damaging the pump bulb 460 from inflating in the wrong position. Also, the second check valve 412 may operate as an anti-auto inflate valve in the deflation position, and creates a type of lockout feature since generating more than 160 psi (or more than 180 psi) of inter-abdominal pressure is highly unlikely. With this type of design the patient can engage in activities or extreme sports (e.g., scuba diving) where bizarre or extreme forces could be placed on the device and the patient could still avoid an un-wanted erection. In some examples, the second check valve 412 is a one-directional pressure check valve that only permits the passage of fluid in one direction. In other examples, the second check valve 412 may include a duckbill valve, a diaphragm check valve, a swing check valve, a tilting disc check valve, a stop-check valve, a lift-check valve, or an in-line check valve.

In some examples, the first check valve 410 and the second check valve 412 may have the same type of valve. In other examples, the first check valve 410 may be a different type than the second check valve 412. In some examples, the second check valve 412 is larger than the first check valve 410.

The spool 408 extends and is movable within the valve body 407 between (and through) the first side opening 490 and the second side opening 479. A user may press the first flexible member 468 (which flexes inwardly) to move the second end portion 474 of the spool 408 in order to place the spool 408 in the inflation position. A user may press the second flexible member 470 (which flexes inwardly) to move the first end portion 472 of the spool 408 in order to place the spool 408 in the inflation position. The movement of the spool 408 within the valve body 407 opens and closes the fluid channels 491-495 (by virtue of the enlarged portions 476 and the reduced portions 478) such that fluid is directed in the correct fluid path to either inflate or deflate the inflatable member 104. For instance, the reduced portions 478 permit the flow of fluid through the spool 408, and the enlarged portions 476 either direct the flow or block the flow of fluid through the spool 408.

When within the inflation position (as shown in FIG. 4E), the position of the spool 408 with respect to the valve body 407 permits the transfer of fluid from the reservoir 102 to the inflatable member 104. For example, when the spool 408 is within the inflation position, the spool 408 connects the fourth fluid channel 494 and the first fluid channel 491 such that fluid can flow through the spool 408 via the reduced portion 478. For example, the release of the pump bulb 460 creates a suction force that opens the first check valve 410 (and closes the second check valve 412) thereby pulling the fluid into the cavity 467 of the pump bulb 460.

Also, when the spool 408 is within the inflation position, the spool 408 connects the second fluid channel 492 with the fifth fluid channel 495 such that fluid can flow through the spool 408 via another reduced portion 478. For example, when the pump bulb 460 is squeezed, the resulting force opens the second check valve 412 (and closes the first check valve 410) such that the fluid can exit the cavity 467 of the pump bulb 460 and flow through the second fluid channel 492 via the second check valve 412. The enlarged portion 476 (e.g., the one in the middle between two adjacent enlarged portions 476) may block the flow of fluid from entering the fourth fluid channel 494. Also, the enlarged portion 476 (e.g., disposed adjacent to the second end portion 474) may block the third fluid channel 493. As the pump continues to be cycled (squeezing and releasing), the fluid is transferred from the reservoir 102 to the inflation member 104 causing an increase in length, size, and pressure. The user continues this cycle until a satisfactory amount of column strength is achieved for intercourse.

In some examples, if the reservoir 102 is at least partially pressurized, the fluid may automatically flow out of the reservoir 102 and into the inflatable member 104 without the user depressing or squeezing the pump bulb 460 until the pressure is at least partially equalized between the reservoir 102 and the inflatable member 104.

In particular, after the spool 408 is switched to the inflation position, the fluid pressure may be greater than the pressure threshold of the first check valve 410 causing the first check valve 410 to transition to its open state such that the fluid can transfer from the reservoir 102 to the pump bulb 460 via the first conduit connector 103, the valve body 407, the first check valve 410. Also, since the fluid pressure is greater than the pressure threshold of the first check valve 410, the second check valve 412 may transition to its open state causing the fluid to transfer from the pump bulb 460 to the inflatable member 104 via the second check valve 412, the valve body 407, and the second conduit connector 105. This automatic transition of fluid continues until the pressure equalizes between the reservoir 102 and the inflatable member 104 (or the first check valve 410 and the second check valve 412 transition to their closed state). The automatic transfer of fluid from the reservoir 102 to the inflatable member 104 (e.g., without the user operating the pump bulb 460) may cause a reduction in the amount of pumps to provide the desired penis rigidity. Also, with added pressure to the reservoir 102, the pump bulb 460 can be filled at a faster rate. As such, it would allow for the feeling of penile engorgement and at least partial filling of the inflatable member 104 (e.g., the cylinders) by a single position selection of the spool 408 when desired by the patient upon arousal. The full final pressurization of the inflatable member 104 may take place with subsequent pump squeezes that would be significantly fewer in number than with devices currently in use.

When the user wants to deflate the inflatable member 104, the user presses the second flexible member 470 causing the second flexible member 470 to flex and move the first end portion 472 of the spool 408, thereby placing the spool 408 in the deflation position (as shown in FIG. 4F). In some examples, the system may automatically transfer fluid until pressures have equalized from the inflatable member 104 to the reservoir 102. For instance, fluid will transfer from the inflatable member 104 and through the second check valve 412 and into the reservoir 102. Once the pressure have equalized, additional fluid can be transferred from the cylinders if the patient squeezes the inflatable member 104. In particular, when within the deflation position, the position of the spool 408 with respect to the valve body 407 permits the transfer of fluid from the inflatable member 104 to the reservoir 102. For example, when the spool 408 is within the deflation position, the spool 408 connects the fifth fluid channel 495 and the third fluid channel 493 such that fluid can flow through the spool 408 via the reduced portion 478. Also, when the spool 408 is within the deflation position, the spool 408 connects the second fluid channel 492 with the fourth fluid channel 494 such that fluid can flow through the spool 408 via another cylindrical portion 478. The enlarged portion 476 (e.g., the one in the middle between two adjacent enlarged portions 476) may direct the flow of fluid into the fourth fluid channel 494 and prevent the flow of fluid into the fifth fluid channel 495. Also, the enlarged portion 476 (e.g., disposed adjacent to the first end portion 472 of the spool 408) may block the first fluid channel 491. As indicated above, the second check valve 412 may operate as an anti-auto inflate valve in the deflation position, and creates a type of lockout feature since generating more than 160 psi (or more than 180 psi) of inter-abdominal pressure is highly unlikely.

Figure 5:
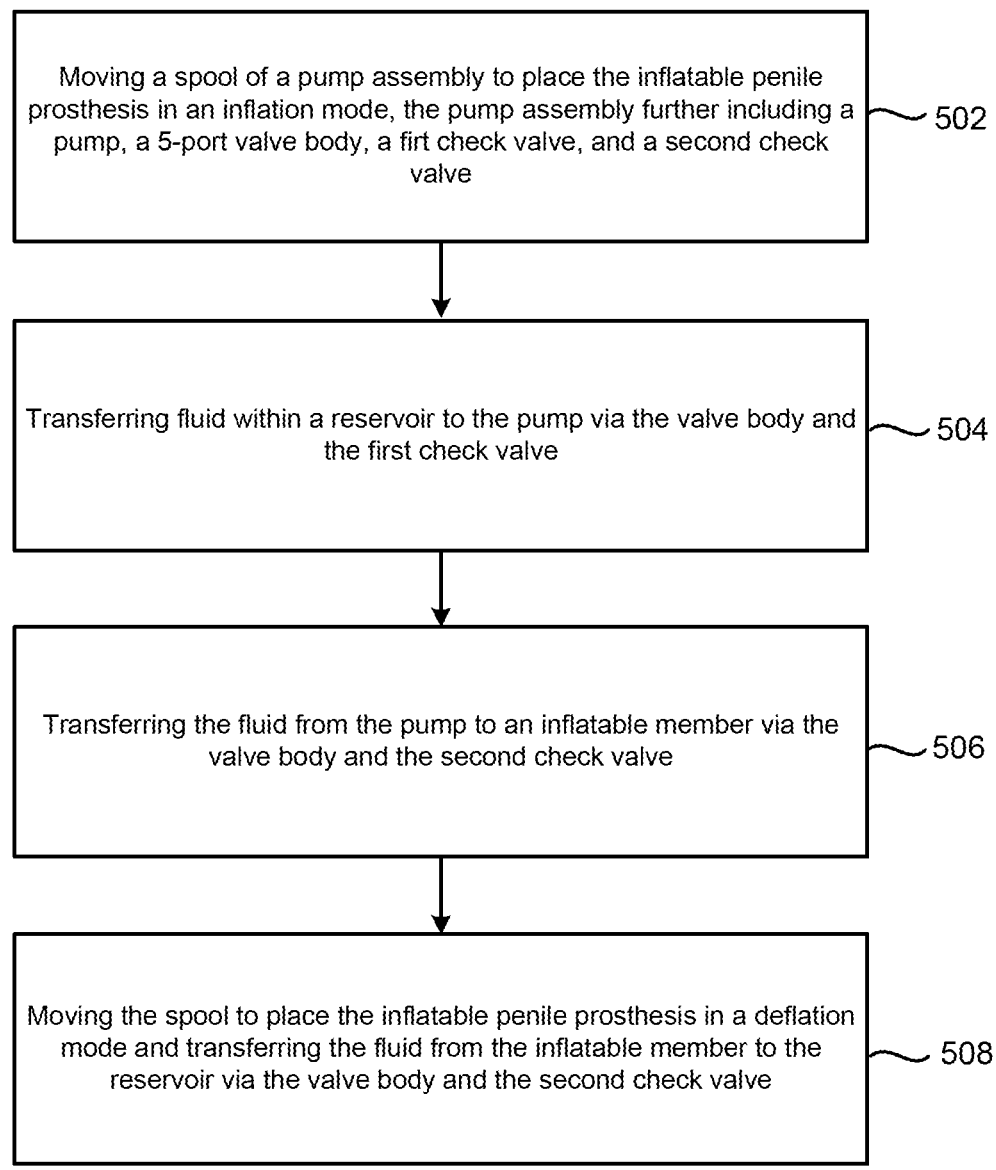
FIG. 5 illustrates a flow chart depicting a method for operating an inflatable penile prosthesis with a reversible flow pump assembly.

FIG. 5 is a flow chart for a method 500 of operating an inflatable penile prosthesis according to an aspect. The operations of the method 500 are explained with reference to the inflatable penile prosthesis 100 of FIG. 1. However, it is noted that the operations of the method 500 may be performed with any of the inflatable penile prostheses described herein.

A spool of a pump assembly may be moved to place the inflatable penile prosthesis in an inflation mode, where the pump assembly further includes a pump, a 5-port valve body, a first check valve, and a second check valve (502). For example, the spool 108 may be moved within a lumen of the valve body 107 to an inflation position. In addition to the spool 108, the pump assembly may include the pump 106 defining a pump bulb and a valve body connector integrally formed with the pump bulb, the valve body 107, the first check valve 110, and the second check valve 112.

Fluid within a reservoir may be transferred to the pump via the valve body and the first check valve (504). For example, release of the pump bulb of the pump 106 may create a suction force that transfers the fluid within the reservoir 102 to the pump 106 via the valve body 107 and the first check valve 110, where the first check valve 110 is open and the second check valve 112 is closed. Fluid may be transferred from the pump to an inflatable member via the valve body and the second check valve (506). For example, when the pump bulb of the pump 106 is depressed, the resulting pressure force may transfer the fluid in the cavity of the pump bulb of the pump 106 to the inflatable member 104 via the valve body 107 and the second check valve 112, where the first check valve 110 is closed and the second check valve 112 is open.

The spool may be moved to place the inflatable penile prosthesis in a deflation mode, and the fluid may be transferred from the inflatable member to the reservoir via the valve body and the second check valve (508). For example, a user may move the spool 108 within the lumen of the valve body 107 to a deflation position. In the deflation position, fluid may automatically be transferred from the inflatable member 104 to the reservoir 102 due to the pressure difference. The fluid may freely enter the pump bulb of the pump 106 via one of the fluid channels, and the position of the spool 108 within the valve body 107 may direct the fluid through the second check valve. Then, the user may squeeze the inflatable member 104 to further transfer the fluid from the inflatable member 104.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis comprising:
    an inflatable member;
    a reservoir configured to hold fluid; and
    a pump assembly configured to facilitate a transfer of the fluid from the reservoir to the inflatable member when in an inflation mode, and facilitate the transfer of the fluid from the inflatable member to the reservoir when in a deflation mode, the pump assembly including:
        a pump;
        a valve body defining a first port, a second port, and a third port operatively coupled to the pump such that three separate fluid channels extend to the pump, the valve body defining a fourth port operatively coupled to the reservoir to transfer fluid to the inflatable member when in the inflation mode, the valve body defining a fifth port operatively coupled to the inflatable member to transfer fluid to the reservoir when in the deflation mode; and
        a spool configured to move within the valve body to switch between the inflation mode and the deflation mode.

2. The inflatable penile prosthesis of claim 1, wherein the three separate fluid channels defined by the valve body include a first fluid channel, a second fluid channel, and a third fluid channel, wherein the pump assembly includes:
    a first check valve disposed within the first fluid channel; and
    a second check valve disposed within the second fluid channel.

3. The inflatable penile prosthesis of claim 2, wherein the third fluid channel is devoid of a check valve.

4. The inflatable penile prosthesis of claim 1, wherein the pump includes a pump bulb.

5. The inflatable penile prosthesis of claim 1, wherein the spool is configured to be manually operated by a user of the inflatable penile prosthesis.

6. The inflatable penile prosthesis of claim 1, wherein the pump includes a pump bulb and a valve body connector integrally formed with the pump bulb, the valve body connector defining a cavity, at least a portion of the valve body being disposed within the cavity of the valve body connector.

7. The inflatable penile prosthesis of claim 1, wherein the spool includes an elongated member having a plurality of enlarged portions and a plurality of reduced portions, wherein at least one of the plurality of enlarged portions is configured to block at least one of the three separate fluid channels in the inflation mode and the deflation mode.

8. The inflatable penile prosthesis of claim 1, wherein the valve body includes a silicone material.

9. The inflatable penile prosthesis of claim 1, wherein the reservoir is pressurized such that activation of the spool to the inflation mode causes at least a portion of the fluid to transfer from the reservoir to the inflatable member through the pump assembly without operating the pump.

10. The inflatable penile prosthesis of claim 1, wherein, when the spool is in the inflation mode, the pump is configured to be depressed causing the fluid to transfer from the reservoir to the inflatable member through the pump assembly.

11. The inflatable penile prosthesis of claim 1, wherein activation of the spool to the deflation mode causes at least a portion of the fluid to transfer from the inflatable member to the reservoir through the pump assembly without operating the pump.

12. The inflatable penile prosthesis of claim 1, wherein the inflatable member includes at least two cylinders.

13. The inflatable penile prosthesis of claim 1, wherein the reservoir includes a biased member configured to pressurize the reservoir.

14. An inflatable penile prosthesis comprising:
    an inflatable member;
    a reservoir configured to hold fluid; and
    a pump assembly configured to facilitate a transfer of the fluid from the reservoir to the inflatable member when in an inflation mode, and facilitate the transfer of the fluid from the inflatable member to the reservoir when in a deflation mode, the pump assembly including:
        a pump defining a pump bulb and a valve body connector integrally formed with the pump bulb, the valve body connector defining a cavity;
        a valve body that is at least partially disposed within the cavity of the valve body connector, the valve body including a first check valve and a second check valve, the valve body includes a first interior portion that defines a first fluid channel, a second fluid channel, and a third fluid channel that extend to the pump bulb, the valve body including a second interior portion that define a fourth fluid channel for transferring the fluid to and from the reservoir and a fifth fluid channel for transferring the fluid to and from the inflatable member; and
        a spool configured to move within a lumen of the valve body to switch between the inflation mode and the deflation mode.

15. The inflatable penile prosthesis of claim 14, wherein the spool has a length longer than a width of the valve body such that a first end portion of the spool extends from one side of the valve body when in the inflation mode and a second end portion of the spool extends from the other side of the valve body when in the deflation mode.

16. The inflatable penile prosthesis of claim 14, wherein the spool being disposed between the first interior portion and the second interior portion.

17. The inflatable penile prosthesis of claim 14, wherein the spool includes an elongated cylindrical member defining a plurality of enlarged cylindrical portions and a plurality of reduced cylindrical portions.

18. A method for operating an inflatable penile prosthesis, the method comprising:
    moving a spool of a pump assembly to place the inflatable penile prosthesis in an inflation mode or a deflation mode, the pump assembly further including a pump and a valve body, the valve body defining a first port, a second port, and a third port operatively coupled to the pump, a fourth port operatively coupled to a reservoir to transfer fluid to an inflatable member, and a fifth port operatively coupled to the inflatable member to transfer fluid to the reservoir;
    during the inflation mode, transferring fluid from the reservoir to the inflatable member via the fourth port to the first port to the second port and through the fifth port; and
    during the deflation mode, transferring fluid from the inflatable member to the reservoir via the fifth port to the third port to the second port and through the fourth port.

19. The method of claim 18, wherein at least a portion of the fluid is transferred from the reservoir to the inflatable member via the pump assembly without operating the pump.

\* \* \* \* \*